United States Patent [19]

Duffy et al.

[11] 4,352,016

[45] Sep. 28, 1982

[54] METHOD AND APPARATUS FOR DETERMINING THE QUALITY OF A SEMICONDUCTOR SURFACE

[75] Inventors: Michael T. Duffy, Princeton Junction; Peter J. Zanzucchi, Lawrenceville, both of N.J.

[73] Assignee: RCA Corporation, New York, N.Y.

[21] Appl. No.: 189,348

[22] Filed: Sep. 22, 1980

[51] Int. Cl.[3] .................... G01N 23/00; G01T 1/22; G01J 1/42

[52] U.S. Cl. .................... 250/358.1; 250/370; 250/372

[58] Field of Search .................... 250/358 R, 359, 360, 250/370, 371, 372; 356/51, 237

[56] References Cited

U.S. PATENT DOCUMENTS

| | | | |
|---|---|---|---|
| 3,451,254 | 6/1969 | Maley | 250/358 |
| 4,211,488 | 7/1980 | Kleinknecht | 356/237 |

OTHER PUBLICATIONS

Zanzucchi, P. J., & Duffy, M. T., "Surface Damage and the Optical Reflectance of Single-Crystal Silicon", *Applied Optics*, vol. 17, No. 21, pp. 3477-3481.

Philipp, H. R. & Taft, E. A., "Optical Constants of Silicon in the Region 1-10 ev", *Physical Review*, vol. 120, No. 1, Oct. 1, 1960, pp. 37-38.

*Primary Examiner*—Alfred E. Smith

*Assistant Examiner*—Janice A. Howell

*Attorney, Agent, or Firm*—Birgit E. Morris; Donald S. Cohen; Joseph D. Lazar

[57] ABSTRACT

The surface quality of a semiconductor material is determined by exposing the semiconductor surface to two light beams of different wavelengths or wavelength ranges (e.g. ultraviolet and near ultraviolet). A portion of each of the respective light beams is reflected from the semiconductor surface. The intensity of each reflected beam is measured to obtain an intensity difference whereby the mangitude of the difference is a measure of the quality of the semiconductor material.

7 Claims, 2 Drawing Figures

METHOD AND APPARATUS FOR DETERMINING THE QUALITY OF A SEMICONDUCTOR SURFACE

BACKGROUND OF THE INVENTION

This invention relates to a method for determining the crystalline quality of material of a semiconductor surface using light.

In manufacturing semiconductor devices, the surface of the semiconductor material in which the devices are fabricated must be substantially free of both physical and crystalline defects. A high degree of crystalline perfection is necessary to produce reliable devices having good electrical properties. In order to control the properties of such devices, it is necessary to be able to determine the quality of semiconductor material that is being used to make the devices.

The light reflectance of the surface of a semiconductor is generally dependent on the physical and crystallographic condition of the surface.

Physical surface damage such as scratches, pits and surface roughness, resulting from lapping and polishing procedures, can be detected by light scattering effects in the visible region of the spectrum for example, by the use of conventional lasers to scan the semiconductor surface. Similarly, the surface texture of homoepitaxial and heteroepitaxial films, prepared on various substrates by chemical vapor deposition (CVD), can also be detected in similar fashion. An example of particular importance is silicon-on-sapphire (SOS). Surface texture or "haze", observed visually because of light scattering, has been attributed in the past to inferior quality SOS material.

Crystallographic damage (or what may be also termed "lattice disorder"), which may also result from lapping and polishing procedures or may be present in homoepitaxial or heteroepitaxial semiconductor films such as SOS, is not easily detected by reflectance methods using visible light. This is due to the fact that the well known "optical" constants of a semiconductor, such as crystalline silicon, are not appreciably influenced by lattice disorder in the visible region of the spectrum. However, the optical constants of silicon are significantly influenced by lattice disorder at photon energies near 4.3 eV which corresponds to the well known $X_4$–$X_1$ silicon transition. This transition occurs at a wavelength of about 2880 angstroms in the ultraviolet region of the spectrum. Thus, the light reflectance of silicon, which is a function of the optical constants, is sensitive to crystalline damage or lattice disorder in the UV region of the spectrum. Other semiconductors display similar reflectance properties at their corresponding characteristic wavelengths.

In view of the above discussion, it is clear that in the semiconductor field there is a need for a fast, nondestructive, quality control method for determining the crystalline quality of semiconductor materials.

SUMMARY OF THE INVENTION

According to the present invention, the crystalline quality of a semiconductor is determined by measuring the light reflectance of the semiconductor at each of two wavelengths, the difference between the respective reflectances being a measure of the crystalline quality of the semiconductor material.

Figure 1:
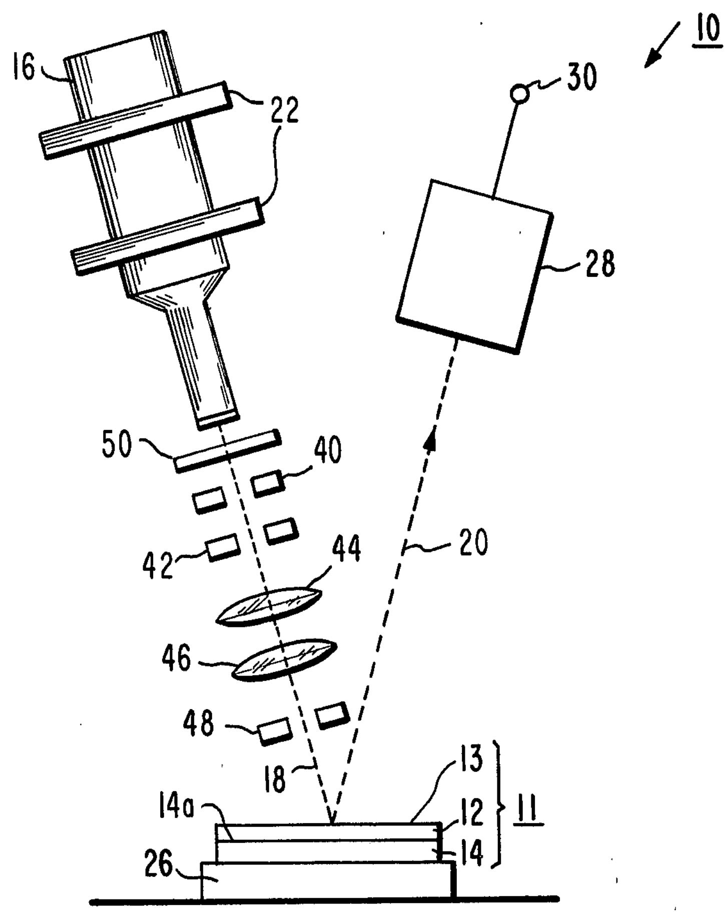
FIG. 1 is a schematic of an apparatus useful in practicing the method of the invention.

The present invention is based on our discovery that the magnitude of the reflectivity of heteroepitaxial silicon films at a wavelength of about 2800 angstroms can be used as a quantitative measure of the quality of SOS films for semiconductor device application. We have discovered that the ultraviolet (UV) reflectivity near this wavelength of about 2800 angstroms correlates very well with device parametric performance and with the results of other physical characterization methods, such as x-ray analysis. In our paper entitled "Surface Damage and the Optical Reflectance of Single-Crystal Silicon", published in Applied Optics, Vol. 17, No. 21, November 1978, pp. 3477–3481, we describe the reflectance of silicon in the photon energy region 2.0 eV to 5.5 eV. If the crystalline perfection (i.e. the quality of the crystalline structure) is degraded, the reflectance in this spectral region is decreased. In principle, the reflectance of a silicon sample relative to a standard reflector, such as an aluminum mirror, at a wavelength of about 2800 angstroms can be used to determine silicon crystalline quality provided surface physical features do not interfere with the measurement.

In practice, the use of the prior art method described in the aforementioned paper proves difficult because of wafer curvature (i.e., warpage), taper and surface texture or roughness. Moreover, a phenomenon known as "haze" in the case of silicon-on-sapphire (SOS) wafers is a commonly known problem relating to light scattering due to surface texture. These effects cause unwanted deflections and/or light scattering in the reflected light which affect the reflected intensity. Thus, the reflected intensity cannot be uniquely attributed to the degree of crystalline perfection of the sample.

According to the present invention, the influence of unwanted deflections and light scattering effects on the measurement of crystalline quality is greatly diminished. By the use of two different selected wavelengths (or ranges of wavelengths) for making the reflectance measurements, the reflectance at one of the wavelengths is sensitive to both the physical and crystalline perfection of the surface while reflectance at the other wavelength (called the reference wavelength) is not as sensitive to the crystalline perfection of the surface but is nevertheless sensitive to the physical perfection of the surface. Accordingly, as shown by the curves illustrated in FIG. 2, to be further described, the reflectance of silicon at a wavelength of, for example, 2800 angstroms is decreased substantially (from about 70% to about 35%) by surface damage (both physical and crystalline) as could be caused, for example, by one micrometer diamond so-called "polishing" grit while the reflectance, for example, at 4000 angstroms is not so strongly affected (i.e., from about 40% to about 35%) because it is less sensitive to crystalline damage. Accordingly, in the embodiment of this invention to be described, the reflectance of a silicon sample at about 4000 angstroms is used as a reference level with which to compare the reflectance of the same silicon sample at a wavelength in practice of about 2800 angstroms. Thus, according to the principles of the present invention, the sample itself becomes its own reference without the need for an external standard as has been heretofore considered necessary.

According to the present invention, both light wavelengths (or wavelength ranges) are emitted by the same source and the corresponding incident light beams subtend the same angle with respect to the same sample. Thus, both reflected beams are influenced in the same manner by the sample curvature and taper.

A suitable apparatus 10 for carrying out the invention is illustrated in FIG. 1. The apparatus 10 provides a means for testing the quality of a sample 11 formed of a semiconductor material 12 deposited on a substrate 14. Sample 11 may be bulk silicon, epitaxial layer on bulk silicon, or silicon films on sapphire or on other substrates such as glass or even metals. The surface 13 of sample 11 is exposed to a beam 18 of ultraviolet (UV) radiation from a source 16. The radiation beam 18 is aimed to strike the surface 13 so that a portion 20 of the beam 18 is reflected from the surface 13. The radiation beam 18 can be provided at either of two wavelengths in a manner to be described. In the present example, the source of ultraviolet radiation used is a conventional hollow-cathode lamp which contains a manganese (Mn) based cathode providing a line spectrum at about 2800 angstroms and about 4050 angstoms. Another source of UV radiation used in this example is a hydrogen lamp emitting a continuum with two band-pass filters, one centered at about 2800 angstoms and the other centered at about 4000 angstroms. However, any suitable source of light 16 to provide suitable wavelengths of light relevant to the semiconductor being evaluated can be used. Source 16 is suitably supported, as by supports 22, within a housing and powered with a suitable power supply (not shown).

The beam of light 18 generated by the source 16 is passed preferably through either of two band-pass light filters 50, a pair of orifices 40 and 42, through a pair of lenses 44 and 46 and thence through another orifice 48. The beam 18 is thus collimated and focused to be incident upon the surface 13. The specimen 11 of semiconductor material 12 is supported on a suitable frame type mounting 26, which may be provided with apparatus for changing the positioning of the semiconductor material 12 relative to the beam 18 so that the beam can scan various portions of the surface 13. The angle of incidence and reflections is no greater than about 10° in order to assume near-normal reflections.

The light from source 16 is preferably filtered with suitable band-pass light filters 50 which are successively positioned in the path of the beam 18 to provide the light of a given predetermined wavelength or wavelength band as desired. In the present embodiment filters 50 are selected to provide light at about 4000 angstroms for one measurement and light at about 2800 angstroms for the second measurement. The apparatus 10 further includes means 28 for measuring the intensity of the reflected beam. Suitably, the measuring means 28 is comprised of a photomultiplier tube or a solid state detector with a suitable power supply.

Figure 2:
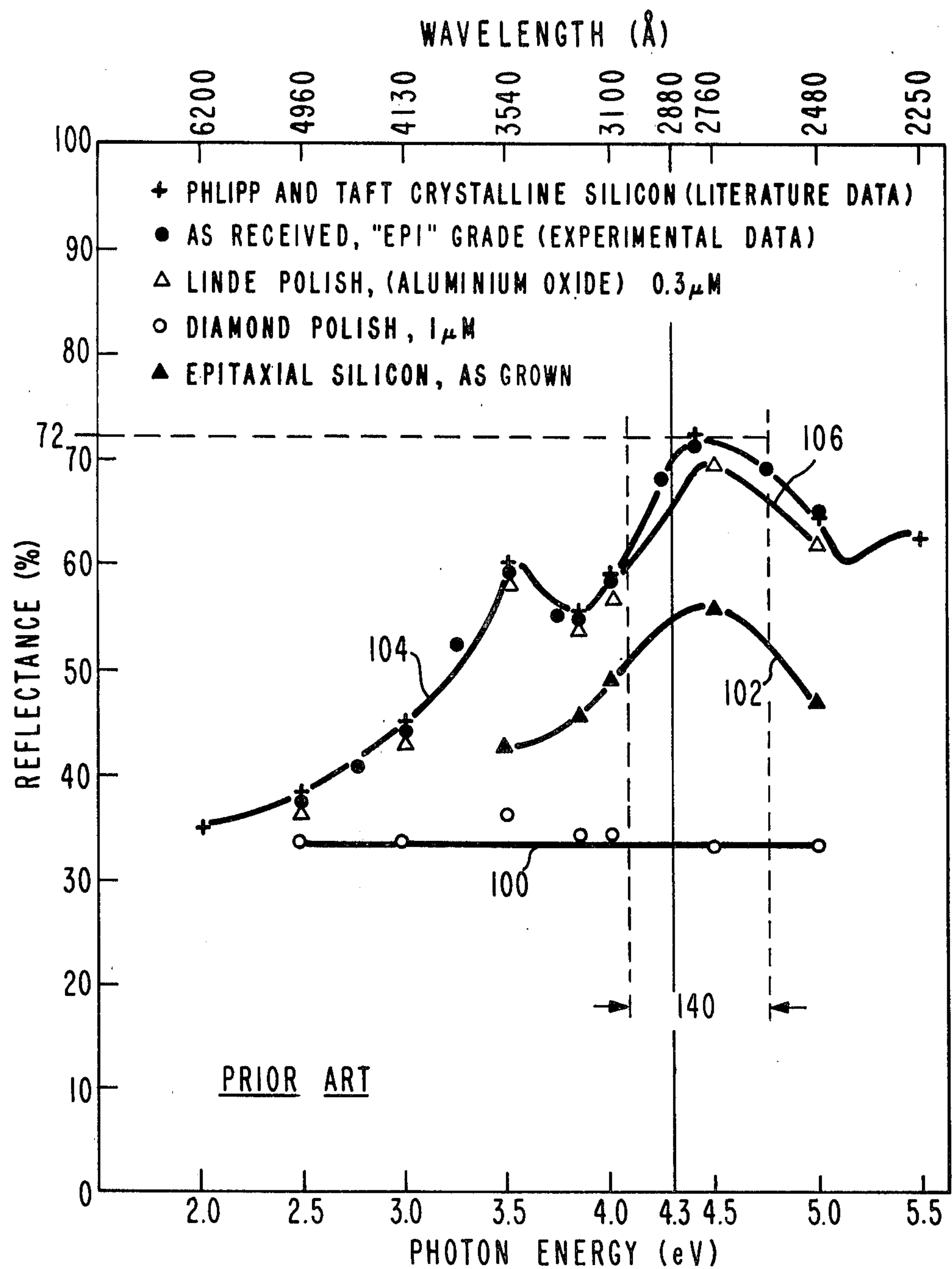
FIG. 2 are curve plots useful in understanding the invention illustrating the reflectance of a single-crystal silicon surface as a function of the photon energy eV and the corresponding wavelength of the incident radiation.

In carrying out the present invention, the semiconductor surface 13 is exposed to the beam 18 of radiation at two different wavelengths, namely at about 4000 angstroms and at about 2800 angstroms in the case of silicon, by suitably selecting filter 50 to provide the desired wavelengths. The beam 18 is reflected from the surface 13 as reflected beam 20. The beam 18 should have suitable wavelengths compatible with the "optical" constants of the particular semiconductor material being tested. One such wavelength is chosen within the wavelength region centered about the relatively high energy for the so-called and well-known "$X_4$–$X_1$" electronic transition in the case of silicon as shown in FIG. 2, to be described, by region 140. The intensity of the reflected beam 20 is measured by the detector 28. Detector 28 provides an intensity signal which appears at terminal 30. This is done for each of the two wavelengths of light. Note that both of the emitted wavelengths of beam 18 are emitted by the same source 16, and moreover, the corresponding incident light beams 18 subtend the same angle with respect to the same sample of material 12. Thus, the reflected radiation 20 at both wavelengths is modified by the sample curvature or warpage and taper in the same manner. Accordingly, the difference in reflectance (ΔR) at the two wavelengths (or wavelength ranges) is equal to $$A-B=\Delta R \quad (1)$$

and is a measure of crystalline quality for the sample being measured, wherein A is the reflectance for light at about 2800 angstroms and B is the reflectance of light at about 4000 angstroms in the case of silicon. The difference in reflectance (ΔR) for a well polished silicon wafer of high crystalline quality can be used to determine the level of perfection attainable. It should be noted, however, that light scattering due to surface roughness or "haze" is a function of wavelength. Since two different wavelengths are involved, the value of ΔR is also modified by surface roughness or "haze" but not nearly so strongly as the measured intensity at either wavelength. Accordingly, the influence of surface roughness on the determination of crystalline quality is greatly diminished.

There are several ways in which the reflectance at the two wavelengths might be compared to each other. For example, the value of ΔR might be normalized according to the following expression:

$$\Delta R'=(A-B)/(B) \quad (2)$$

wherein A and B are the reflectances as defined above for equation (1) and $\Delta R'=(\Delta R)/B$. The larger the values of ΔR and ΔR′, the better the quality of the sample being evaluated. For well polished silicon, the value ΔR is about 0.22 and the value of ΔR′ is about 0.46. Smaller values than these represent inferior quality silicon. The values of the two wavelengths selected for the characterization of a silicon sample can be different from the specific values of 2800 angstroms and 4000 angstroms discussed above. However, for evaluation of silicon films on sapphire, the reference wavelength should not be greater than about 4000 angstroms because some light penetrating the silicon film 12 at the selected reference wavelength may be reflected at the surface **14*a*** of the sapphire and cause unwanted light interference effects in the specularly reflected light. This phenomenon depends upon the thickness of the silicon film used. Note that the reference wavelength could be less than 4000 angstroms. Moreover, in the evaluation of polished silicon wafers, the reference wavelength can be greater than 4000 angstroms since interference effects do not occur. The reference wavelength could also be chosen at shorter wavelengths than 2800 angstroms, for example 2000 angstroms, for the evaluation of silicon.

The penetration depth for radiation at a wavelength of about 2800 angstroms is limited to a surface layer of silicon which may be as thin as about 100 angstroms or less. Consequently, the light reflectance technique according to the present invention for the characterization of silicon is related principally to a shallow surface layer of material of about 50 angstroms in thickness.

In the embodiment of the invention being described, the evaluation of single crystal silicon in our experiments is done primarily in accordance with equation (1). However, equation (2) has also been used in the evaluation of single crystal, polycrystalline and amorphous silicon. The intensity signal at terminal 30 can be recorded for each measurement or suitable apparatus may be provided to record and store the intensity signals and provide a difference signal by a suitable comparative computation. Nevertheless, it will be appreciated that the respective reflectances can be, for example, related as ratios rather than arithmetic differences as exemplified by equations (1) and (2).

FIG. 2 shows a plot of several reflectance curves disclosed in the above-identified "Applied Optics" paper. The reflectance characteristics plotted against the photon energy (eV) and corresponding wavelength of reflected light makes clear how the reflectance of silicon varies with the wavelength and the corresponding photon energy of the reflected light. These curve plots (FIG. 2) will be used in the discussion to follow hereinafter. Curve 100 represents the reflectance from a silicon wafer that has been polished with diamond. It will be noticed that the reflectance for curve 100 is substantially constant. Thus, there is no dependence of reflectance on wavelength in the region of photon energies between 2.5 and 5 eV. Curve 102 is a plot of the reflectance characteristics of the surface of epitaxial silicon as grown by an epitaxial process. It will be noticed that curve 102 rises from a reflectance of about 40% at 3.5 eV and peaks at about 55% near 4.5 eV and then droops off to about 45% as it approaches 5.0 eV. Curve 104 is a plot of data from several sources. It includes literature data as reported by Phillip and Taft determining the reflectivity characteristics of crystalline silicon. The solid dots of curve 104 are the experimental data determined by us as explained in the above-identified article "Applied Optics", Vol. 17. Curve 106 represents our results on the reflectivity of silicon that has been polished with aluminum oxide otherwise known as Linde polish in which the grit size of the aluminum oxide is 0.3 microns. Curve 106 displays diminished reflectance due to polishing damage particularly in the region near 4.5 eV. What should be noticed in regard of the curves 100, 102, 104 and 106 is that along the substantially common ordinate near 4.5 eV within the region 140 there is a difference in the reflectance that manifests different degrees of discernible surface damage.

The reflectance curve 104 in FIG. 2 shows an increase in reflectance from about 35% at 2.0 eV to a maximum of about 72% at a photon energy of about 4.5 eV. Other semiconductors have similar characteristic curves. The photon energy in electron volts (eV) is related to the corresponding wavelength of light by the relationship:

$$\epsilon\lambda = hc = 1.24 \quad (3)$$

where $\epsilon$ is the photon energy in eV (electron volts), $\lambda$ is the wavelength in micrometers, h is Planck's constant and c is the velocity of light.

In the plots in FIG. 2 of the reflectance characteristics for silicon, we have observed that reflectance in the spectral region centered about 2800 angstroms, designated region 140 for convenience, is diminished due to surface damage and inferior surface crystalline quality as demonstrated for the case of 1 $\mu$m diamond grit abrasion (curve 100) and also in the case of "as-grown" epitaxial silicon (curve 102). The UV reflectance of silicon measured in region 140, it should be understood, gives information very different from reflectance measured in the visible region of the spectrum such as measured by commercial laser scanners. Similar considerations apply to optical reflectance methods on semiconductor materials other than silicon. For example, the region 140 of a similar but relevant curve 104 for germanium is centered at about 4.5 eV which corresponds to UV radiation having a wavelength of about 2760 angstroms. For gallium arsenide, region 140 is centered about 5.0 eV for a UV wavelength of about 2480 angstroms. In the case of both germanium and gallium arsenide it is expected that light at 4000 angstroms will serve as an adequate reference. Further investigations of these semiconductors may point to a better reference wavelength of light.

According to the process of the present invention, one can determine the crystalline quality of these semiconductors. Reduced reflectance is in all cases related to reduced surface physical perfection and reduced surface crystalline perfection and these two latter properties can be largely separated by the two-wavelength measurement method according to this invention using appropriate wavelengths for each semiconductor. The present invention lends itself to a non-destructive, fast, simple and sensitive means for determining the quality of a semiconductor material. The semiconductor surface can be evaluated for crystalline quality prior to the manufacture of devices, thereby eliminating the costly continuation of device processing inferior semiconductor material. In particular, it can be used for bulk silicon, homoepitaxial silicon or heteroepitaxial silicon and, at relevant wavelengths, the technique can be used to evaluate the surface quality of semiconductor materials other than silicon, such as germanium and gallium arsenide.

What is claimed is:

1. A method of determining the surface quality of a semiconductor material comprising:

(a) exposing said semiconductor surface to a first beam of radiation of a first wavelength from a source of radiation at a preselected angle of incidence so that a portion of said first beam is reflected from said surface;

(b) measuring the intensity of said reflected beam to obtain a first intensity signal;

(c) thereafter exposing said semiconductor surface to a second beam of radiation from said source at said angle so that a portion of said second beam is reflected from said surface, said second beam having a wavelength different from the wavelength of said first radiation beam, the wavelength of one of said beams being in the ultra-violet spectrum region wherein the influence of crystal lattice disorder of the material on reflectance is significantly greater than the influence of crystal lattice disorder on reflectance of said material at the other wavelength;

(d) measuring the intensity of said second reflected beam to obtain a second intensity signal; and (e) comparing said first intensity signal with said second intensity signal to determine the difference between the two signals, the magnitude of said difference being a measure of quality of said semiconductor material.

2. The method of claim 1 wherein the material is silicon and exposing the silicon to the first beam at about 2800 angstroms and to the second beam at about 4000 angstroms.

3. The method of claim 1 wherein the semiconductor material exhibits a light reflectance response characteristic having a maximum value of reflectance and further comprising the step of selecting the first beam with a wavelength corresponding substantially to the maximum reflectance value.

4. The method of claim 1 wherein each of said first and second wavelengths are included respectively in a first and second range of wavelengths.

5. The method of claim 1 wherein the semiconductor material is gallium arsenide and further comprising the step of selecting the first beam with a wavelength of 2480 angstroms and the second beam with a wavelength of about 4000 angstroms.

6. The method of claim 1 wherein the semiconductor material is germanium and further comprising the step of selecting the first beam with a wavelength of 2760 angstroms and the second beam with a wavelength of about 4000 angstroms.

7. Apparatus for testing the surface quality of a semiconductor material comprising:

(a) means for exposing said semiconductor surface to a first beam of radiation of a first wavelength from a source of radiation at a preselected angle of incidence, so that a portion of said first beam is reflected from said surface;

(b) means for exposing said semiconductor surface thereafter to a second beam of radiation from said source at said angle having a second wavelength different from said first radiation so that a portion of said second beam is reflected from said surface, the wavelength of one of said beams being in the ultra-violet spectrum region wherein the influence of crystal lattice disorder of the material on reflectance is significantly greater than the influence of crystal lattice disorder on reflectance of said material at the other wavelength;

(c) means for measuring the intensity of said first and second reflected beams to obtain a first intensity signal and a second intensity signal; and (d) means for displaying indicia corresponding to said first intensity signal and said second intensity signal to provide information to obtain the intensity difference, the magnitude of said intensity difference being a measure of quality of said semiconductor material.

* * * * *